US009625325B2

(12) United States Patent
Bickford et al.

(10) Patent No.: US 9,625,325 B2
(45) Date of Patent: Apr. 18, 2017

(54) SYSTEM AND METHOD FOR IDENTIFYING OPERATING TEMPERATURES AND MODIFYING OF INTEGRATED CIRCUITS (71) Applicant: GLOBALFOUNDRIES INC., Grand Cayman (KY)

(72) Inventors: Jeanne P. Bickford, Essex Junction, VT (US); Nazmul Habib, Essex Junction, VT (US); Baozhen Li, Essex Junction, VT (US); Tad J. Wilder, South Hero, VT (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 14/624,907

(22) Filed: Feb. 18, 2015

(65) Prior Publication Data
US 2016/0240479 A1    Aug. 18, 2016

(51) Int. Cl.
*G01R 31/26* (2014.01)
*G01K 7/16* (2006.01)
*G01L 21/30* (2006.01)
*G01R 31/00* (2006.01)
*G01N 27/64* (2006.01)
*G01N 27/62* (2006.01)
*G01N 17/00* (2006.01)
*G01N 27/82* (2006.01)
*G01R 33/12* (2006.01)
*G01N 27/74* (2006.01)
(Continued)

(52) U.S. Cl.
CPC ............... *G01K 7/16* (2013.01); *G01L 21/30* (2013.01); *G01N 17/00* (2013.01); *G01N 27/62* (2013.01); *G01N 27/64* (2013.01); *G01R 31/00* (2013.01); *H01J 41/00* (2013.01); *H01J 41/02* (2013.01)

(58) Field of Classification Search
CPC ........ G01N 17/00; G01N 27/62; G01N 27/64; G01R 31/26; G01R 31/2642; G01R 31/2648; G01R 31/2831; G01R 31/31702; G01R 31/00; G01L 21/30; H01J 41/00; H01J 41/02
USPC .......... 324/76.11–76.83, 439, 459, 500, 549, 324/600, 649, 691, 719, 762.01, 200–263
See application file for complete search history.

(56) References Cited

U.S. PATENT DOCUMENTS

5,154,514 A    10/1992   Gambino et al.
5,639,163 A     6/1997   Davidson et al.
6,019,508 A     2/2000   Lien
(Continued)

*Primary Examiner* — Huy Q Phan
*Assistant Examiner* — Raul Rios Russo
(74) *Attorney, Agent, or Firm* — David Cain; Hoffman Warnick LLC (57) ABSTRACT

Aspects of the present disclosure include a computer-implemented method for identifying an operating temperature of an integrated circuit (IC), the method including using a computing device for: applying a test voltage to a test circuit embedded within the IC, the test circuit including a phase shift memory (PSM) element therein, wherein the PSM element crystallizes at a crystallization temperature from an amorphous phase having a first electrical resistance into a crystalline phase having a second electrical resistance, the second electrical resistance being less than the first electrical resistance; and identifying the IC as having operated above the crystallization temperature in response to a resistance of the test circuit at the test voltage being outside of the target operating range.

20 Claims, 6 Drawing Sheets (51) Int. Cl.
  *H01J 41/02* (2006.01)
  *H01J 41/00* (2006.01)

(56) References Cited

U.S. PATENT DOCUMENTS

| | | |
|---|---|---|
| 7,020,014 B2 | 3/2006 | Khouri et al. |
| 7,123,995 B1 | 10/2006 | Desai et al. |
| 7,882,455 B2 | 2/2011 | Habib et al. |
| 8,114,686 B2 | 2/2012 | Habib et al. |
| 8,259,488 B1 | 9/2012 | Tedrow et al. |
| 2003/0082842 A1 | 5/2003 | Hwu et al. |
| 2003/0214998 A1 | 11/2003 | Gauthier et al. |
| 2004/0151023 A1 | 8/2004 | Khouri et al. |
| 2005/0166166 A1 | 7/2005 | Chandra et al. |
| 2006/0111865 A1 | 5/2006 | Choi |
| 2006/0198183 A1* | 9/2006 | Kawahara ............... G11C 29/50 365/163 |
| 2008/0117697 A1* | 5/2008 | Philipp ............... G11C 13/0004 365/201 |
| 2008/0231295 A1* | 9/2008 | Ruf .................. G01R 31/31905 324/754.07 |
| 2009/0001336 A1 | 1/2009 | Habib et al. |
| 2010/0244023 A1* | 9/2010 | Parkinnson ............ G11C 29/24 257/48 |
| 2011/0155992 A1* | 6/2011 | Kao .................. G11C 13/0004 257/4 |
| 2011/0317480 A1* | 12/2011 | Lung ................. G11C 13/0004 365/163 |

* cited by examiner

FIG. 6

SYSTEM AND METHOD FOR IDENTIFYING OPERATING TEMPERATURES AND MODIFYING OF INTEGRATED CIRCUITS

BACKGROUND

Aspects of the invention relate generally to systems and methods for identifying operating temperatures and/or modifying of integrated circuits (ICs). More specifically, embodiments of the present disclosure can identify features of an IC which have experienced operating temperatures above a particular value, and can modify the operation of an IC by the use of temperature treatments.

Each IC of a particular device can be made up of millions of interconnected devices, such as transistors, resistors, capacitors, and diodes, located on one or more chips of semiconductor substrate material. Computer-implemented solutions such as manufacturing models can at least partially govern the design, fabrication, and other processing steps of IC components used in a given device. Conventional manufacturing models may rely upon predicted values of temperature and/or voltage during deployment. These predicted values are also known as the specification, design, and/or nominal operating temperature or voltage. These temperatures and/or voltages are typically set at the time of design to predict performance attributes such as a total operating time of the IC after being manufactured and deployed.

Actual operating conditions (e.g., temperatures and voltages) of a device can vary significantly from their predicted conditions. These variations can alter the field viability of a device which includes ICs therein. In addition, an IC of a product may be subject to unauthorized tampering and/or modification after being deployed. For example, some IC components may be removed from a corresponding card, or may undergo "cosmetic" repairs which can negatively affect the performance of an underlying feature or module. Thus, the true quality of a device may differ from what the manufacturing model of its manufacturing line predicts.

SUMMARY

A first aspect of the present disclosure provides a computer-implemented method for identifying an operating temperature of an integrated circuit (IC), the method comprising using a computing device to perform actions including: applying a test voltage to a test circuit embedded within the IC, the test circuit including a phase shift memory (PSM) element therein, wherein the PSM element crystallizes at a crystallization temperature from an amorphous phase having a first electrical resistance into a crystalline phase having a second electrical resistance, the second electrical resistance being less than the first electrical resistance; and identifying the IC as having operated above the crystallization temperature in response to a resistance of the test circuit at the test voltage being outside of the target operating range.

A second aspect of the present disclosure provides a system for identifying an operating temperature of an integrated circuit (IC), the system comprising: a test circuit embedded within the IC, the test circuit including a phase shift memory (PSM) element therein, wherein the PSM element crystallizes at a crystallization temperature from an amorphous phase having a first electrical resistance into a crystalline phase having a second electrical resistance, the second electrical resistance being less than the first electrical resistance; and a controller electrically connected to the test circuit and configured to perform actions including: determining a resistance of the test circuit; comparing the resistance of the test circuit with a target operating range, and identifying the IC as having operated above the crystallization temperature in response to the resistance of the test circuit being outside of the target operating range.

A third aspect of the present disclosure provides a method for modifying an integrated circuit (IC) unit, the method comprising: providing an IC having a phase shift memory (PSM) element therein; heating the PSM element of the IC to a crystallization temperature, the PSM element being electrically connected to at least one electrical component of the IC, wherein the PSM element crystallizes at the crystallization temperature from an amorphous phase having a first electrical resistance into a crystalline phase having a second electrical resistance, the second electrical resistance being less than the first electrical resistance, wherein the IC with PSM element in the crystalline phase provides a modified circuit operation.

BRIEF DESCRIPTION OF THE SEVERAL VIEWS OF THE DRAWINGS

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings, and it is to be understood that other embodiments may be used and that changes may be made without departing from the scope of the present teachings. The following description is, therefore, merely illustrative.

Embodiments of the present disclosure provide a system for identifying operating temperatures of an integrated circuit (IC). The process of identifying operating temperatures can include determining whether circuit elements have, at one instance in time, operated at a temperature outside of a target range of temperatures. Identifying the operating temperatures of an IC can illustrate the operating conditions of individual features or particular constructions within an IC, such as voltage islands, high frequency circuits, locations of an IC with high concentrations of structures, and/or dense wiring areas.

A system for identifying the operating temperatures of an IC according to embodiments of the present disclosure can include a test circuit embedded within the IC. The test circuit can include a phase shift memory (PSM) element electrically connected to other elements of the IC. A PSM element is defined as any material with electrical properties which can change based on the phase of matter of its underlying composition. As discussed herein, a change in the PSM element's phase of matter can affect the electrical properties of the material in addition to the behavior of the IC where the PSM element is used. In addition, the PSM element's altered electrical properties can remain intact even after the PSM element returns to its original temperature. PSM elements composed of the materials described herein can be manufactured in a size which causes no appreciable impact to the structure and contents of a particular IC.

In embodiments of the present disclosure, the composition of a PSM element can transition from an amorphous phase (with a corresponding first resistance) into a crystalline phase (with a corresponding second, typically lower resistance) upon reaching a crystallization temperature. Measuring the resistance of the test circuit to measure electrical resistance of the IC can indicate whether one or more of its PSM elements have become crystalline. The presence of a crystalized PSM element can indicate that the IC has previously experienced an operating temperature above the crystallization temperature. Where applicable, the crystallization temperature of the PSM element can represent an upper limit of desired operating temperatures for the IC. The material composition of the PSM element, including the presence or absence of additives, can determine the crystallization temperature of the PSM element. The resistance of the PSM element under a particular voltage can depend on whether the device has previously operated above the crystallization temperature. Temperature spikes may occur during one of several events or conditions after an IC is deployed, e.g., wafer tests, module build processes, module tests, burn-in environment operation, system level tests, and conventional operating settings.

Figure 1:
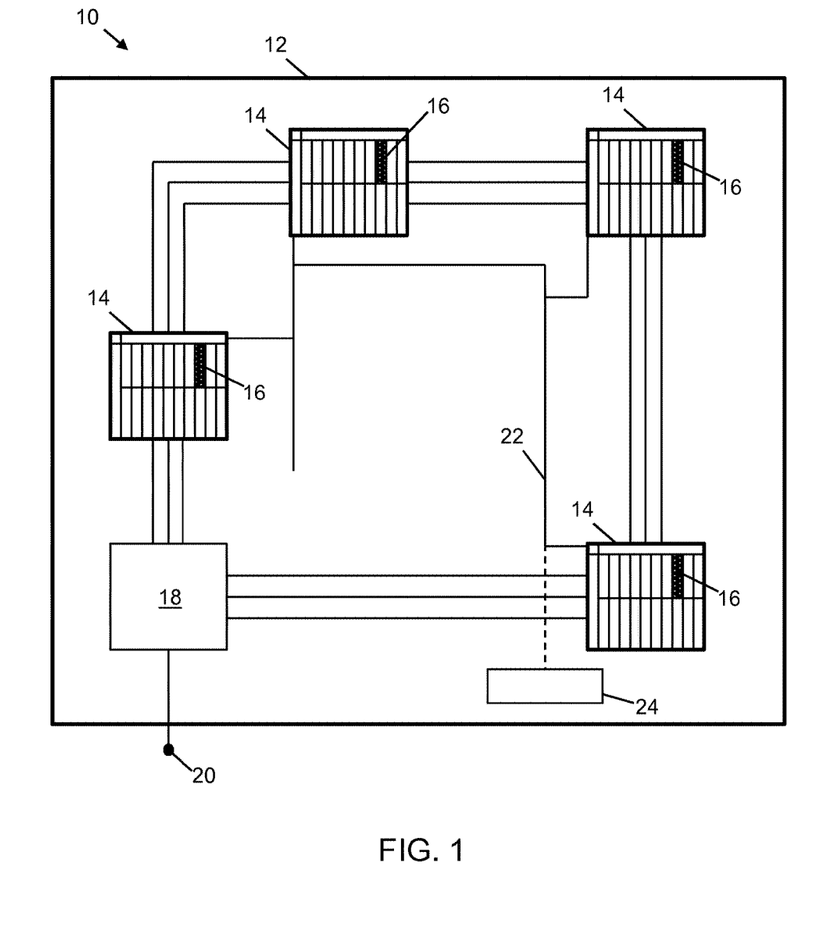
FIG. 1 provides a schematic view of a system according to embodiments of the present disclosure.

Turning to FIG. 1, a system 10 according to embodiments of the present disclosure is shown. An integrated circuit (IC) 12 of system 10 can include one or more test circuits 14, each of which can be embedded within a different location of IC 12. IC 12 can be contained entirely within one device provided to an end user, or can represent only part of a device which includes multiple ICs 12 or portions thereof. One or more test circuits 14 of system 10 can include a phase shift memory (PSM) element 16 therein. PSM element 16 can be an at least partially electrically conductive material coupled to other circuit elements, e.g., by connecting instruments such as metal level layers, wires, etc. Except for temperature and phase-dependent properties discussed herein, PSM element 16 can generally function as a direct electrical connection between two or more nodes, components, contacts, features, etc. In other embodiments, PSM element 16 can function as an electrical fuse, programmable by way of temperature treatments. As used herein, a "programmable" component or fuse can constitute an electrical connection between two components of an IC which may be rendered non-conductive by the action of a user or another circuit element. Programming the fuse, also known as "fusing" the fuse, can refer to any process for rendering an electrically conductive component or connection substantially non-conductive. Embodiments of the present disclosure can relate to the fusing of PSM element(s) 16 by performing one or more temperature treatments.

The composition of PSM element 16 can include, e.g., germanium antimony (GeSb), germanium-antimony-tellerium (GST), or combinations of these materials with each other and/or other materials. PSM element(s) 16 can further include dopants. To adjust properties such as crystallization temperature and the relationship between resistance and temperature for PSM element 16, the composition of PSM element 16 can include dopants such as nitrogen (N), silicon (Si), and/or ionic compounds such as silicon nitride (SiN) therein. As is known in the art, "doping" refers to a process by which an impurity or "dopant" is introduced into a semiconductive material to alter its electrical properties, e.g., the conductivity and resistivity of a material.

Each test circuit 14 can be electrically connected to a clock controller 18, which in turn can be electrically coupled to a clock wire 20 for providing electrical signals to system 10. Clock controller 18 can direct signals from clock wire 20 to one or more of test circuits 14 based on instructions (e.g., algorithms, logic instructions, and/or other encoded guidelines) defined within controller 18. A test wire 22 can also electrically connect one or more test circuits 14 to a controller 24. Controller 24 can be in the form of any currently known or later developed instrument for sending or receiving electrical signals throughout an IC, and capable of measuring and/or determining related quantities such as voltages, currents, etc. Controller 24 can be connected to or function as a multimeter (a multipurpose electrical measurement device including, e.g., voltmeter and/or ammeter settings or functions), a clock generator, or any other device for transmitting electrical signals and/or measuring electrical attributes. Controller 24 can also include or otherwise be communicatively connected to a computing device or other system configured to perform a group of method steps as detailed herein. Test wires 22 can also be in the form of a bus or fat wire connection between test circuits 14 and controller 24 to provide multiple return signals to controller 24, and measure multiple test circuits 14 sequentially and/or simultaneously.

Figure 2:
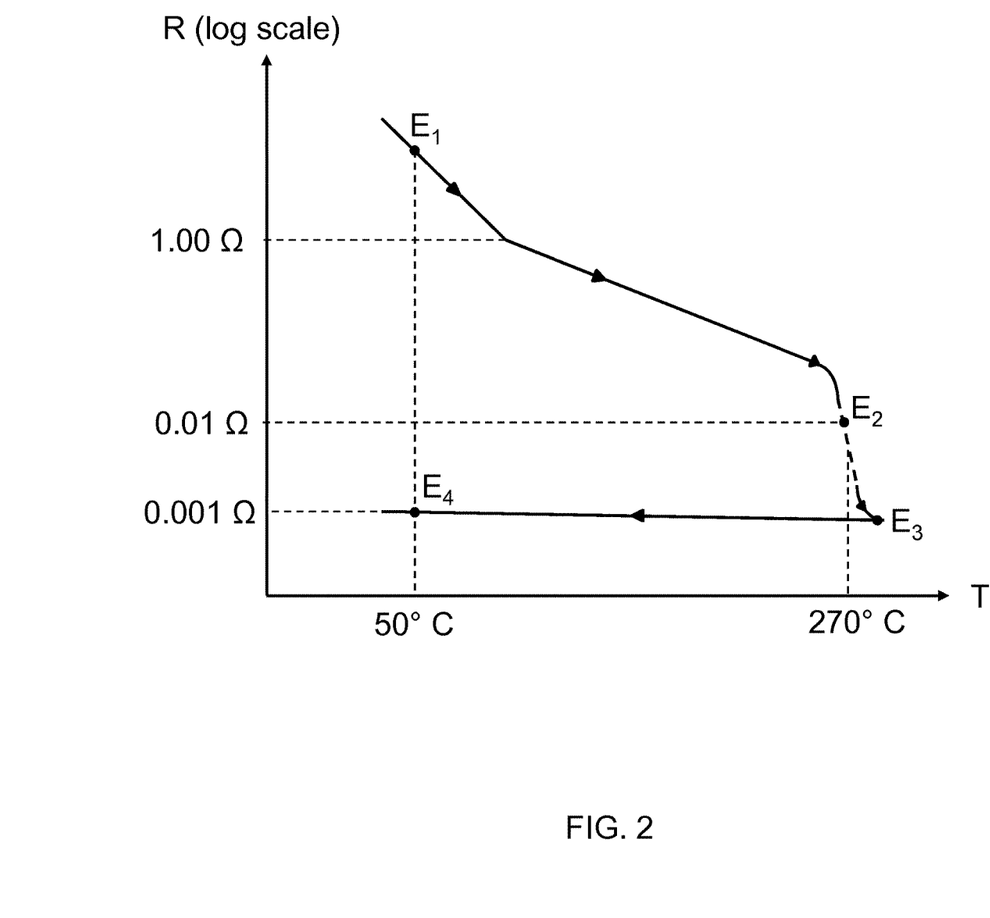
FIG. 2 is a plot of a parametric curve of resistance and temperature over time for a PSM element according to embodiments of the present disclosure.

In operation, changes to the electrical properties of PSM element 16 can provide a mechanism for identifying whether IC 12 and/or components thereof have previously operated above the crystallization temperature of PSM element 16. Referring to FIGS. 1 and 2 together, a parametric curve of resistance and temperature for one PSM element 16 is shown as an example. Four reference points in time, $E_1$, $E_2$, $E_3$, and $E_4$, represent four stages during an operation where PSM element 16 is heated from a first temperature (i.e., approximately 50° C.) to a second temperature (i.e., approximately 270° C.), and then cooled back to the first temperature. The parametric curve of FIG. 2 provides measurements of resistance for PSM element 16 plotted on a logarithmic scale to better illustrate differences between orders of magnitude. At point $E_1$, PSM element 16 (FIG. 1) can be in an amorphous phase. That is, the material composition of the PSM element 16 can be condensed, solid, and non-crystalline. In the amorphous phase at a temperature of 50° Celsius (C), the composition of PSM element 16 can have an electrical resistance of at least approximately 1.00 Ohms (Ω). In a test circuit (e.g., test circuit 14 (FIG. 1)), the resistance of PSM element 16 in the amorphous phase can correspond to a "high voltage," as current passes through PSM element 16.

In FIG. 2, PSM element 16 is shown to be heated to a temperature of approximately 270° C. at point $E_2$. As temperature of PSM element 16 (FIG. 1) increases between points $E_1$ and $E_2$, the resistance of the PSM element can decline according to an inversely proportionate relationship, and may be piecewise defined with different rates of declining resistance as is shown in FIG. 2. The temperature of the PSM element at $E_2$ can correspond to a crystallization temperature for the material (e.g., approximately 270° C.). At the crystallization temperature, the further transfer of heat into PSM element 16 can cause its material composition to begin crystallizing. As more heat is added to test circuit 14 (FIG. 1), PSM element 16 can crystallize from its initial, amorphous phase into a crystalline phase. In the crystalline phase, PSM element 16 can remain solid, but the bonding within its internal structure can take on the structure of a crystal lattice, thereby becoming less condensed. Before crystallization of PSM element 16 begins at point $E_2$, the electrical resistance of PSM element 16 can be inversely related to temperature. As the heating of PSM element 16 continues to point $E_3$, the material composition of PSM element 16 can substantially fully crystallize (i.e., at least 99% of PSM element 16 becomes crystallized in the example of FIG. 2). The temperature change of PSM element 16 between the amorphous state and substantially full crystallization can correspond to a temperature change of, e.g., approximately 10° C. As shown in FIG. 2, the crystallizing of PSM element 16 between points $E_2$ and $E_3$ can cause a sharp decline in the resistance of PSM element 16, e.g., between approximately 0.01Ω and approximately 0.001Ω. After the PSM element 16 substantially crystallizes, the heat source can be reheated or removed and the temperature can return to approximately 50° C. between points $E_3$ and $E_4$ as shown in FIG. 2. After PSM element 16 substantially crystallizes at point $E_3$, further temperature changes can cause negligible effect on the resistance of PSM element 16, as indicated by the resistance remaining constant at approximately 0.001Ω between points $E_3$ and $E_4$ in FIG. 2.

According to the parametric curve illustrated in FIG. 2, PSM element 16 can become substantially electrically conductive after crystallizing. The lower electrical resistance of PSM element 16 after crystallization (i.e., approximately 0.001Ω as shown in FIG. 2) can generally correspond to a "low voltage" value or a zero in a digital logic circuit. The crystallizing of PSM element 16, e.g., as shown between points $E_2$ and $E_3$ of FIG. 2, in operation may occur when IC 12 is subject to a temperature which exceeds the crystallization temperature of PSM element 16. Using PSM element(s) 16 with a crystallization temperature which approximates the upper limit on a device's operating temperature can provide temperature identification features. Specifically, the high voltage or low voltage properties of PSM element 16 during operation can allow controller 24 (FIG. 1) to identify whether IC 12 previously operated above the crystallization temperature. The corresponding change in resistance of PSM element(s) 16 can also provide a modified operation of IC 12, similar to blowing a fuse, as discussed elsewhere herein. Reheating the PSM element 16 to temperatures much greater than the crystallization temperature (e.g., above 600° C. in the case of GeSb) after PSM element 16 crystallizes can liquefy or evaporate the composition of PSM element 16. The evaporated or liquefied material may become amorphous after solidifying and/or after undergoing further process steps. Thus, PSM element 16 in some instances can return to its amorphous phase by applying different temperature treatments.

Figure 3:
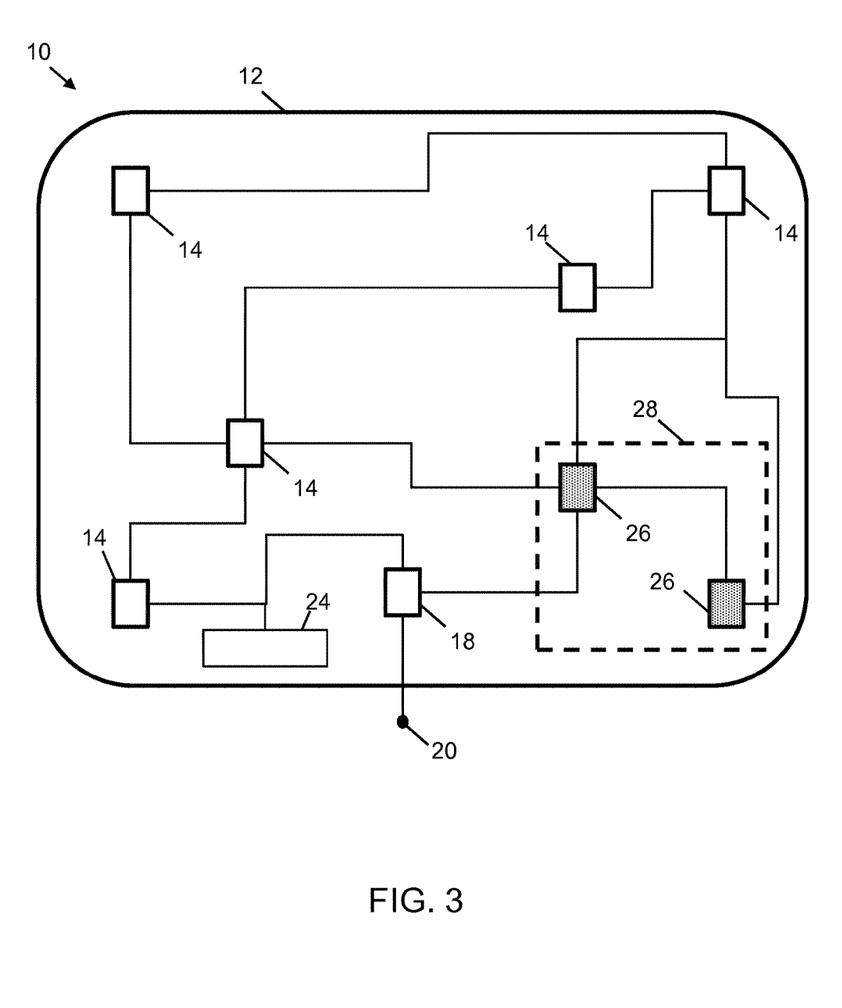
FIG. 3 provides a schematic view of a system including amorphous and crystallized PSM elements according to embodiments of the present disclosure.

Referring to FIG. 3, another illustration of system 10 is provided to demonstrate processes for identifying operating temperatures according to embodiments of the present disclosure. IC 12 can include multiple test circuits 14 located at corresponding test sites of IC 12. Each test site with a corresponding test circuit 14 can be a location of interest, or a location which may be subject to temperatures above the crystallization temperature. During the operation of IC 12, one or more test sites may experience operating temperatures above the crystallization temperature of a particular PSM element 16 (FIG. 1). Where PSM elements 16 crystallize, the corresponding test circuits 14 can become modified test circuits 26.

Several modified test circuits 26 can be concentrated in a particular area of IC 12 after a period of operation. Other test circuits 14 which have not operated above the crystallization temperature may not include crystallized PSM elements 16 therein. Modified test circuits 26 in close proximity to each other, e.g., adjacent modified test circuits 26 without other test circuits 14 between them, can be grouped together to define a hot spot 28 of IC 12. A "hot spot" refers to a region of IC 12 where one or more crystallized PSM elements 16 are present. Each hot spot 28 can identify a corresponding area of IC 12 which has experienced a temperature above the crystallization temperature for PSM element(s) 16. Calculating a temperature gradient for IC 12 can include locating modified test circuits 26 and/or hot spots 28 of IC 12.

Figure 4:
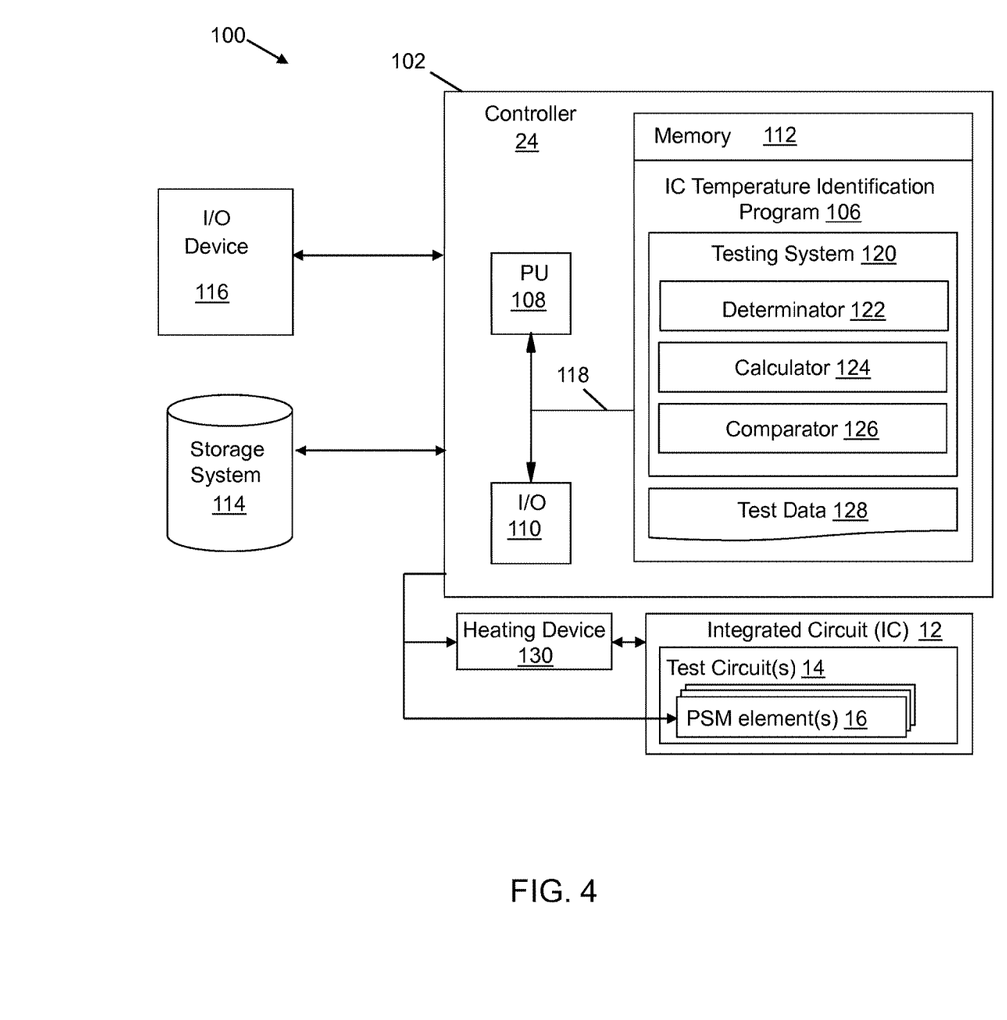
FIG. 4 provides a schematic view of an illustrative environment for performing a method or operating a system according to embodiments of the present disclosure.

Turning now to FIG. 4, an illustrative environment 100 for implementing the method and/or system described herein is shown. The method and/or system may be coded as a set of instructions on removable or hard media for use by a general-purpose computer, and thus may, in embodiments, include a computer program product. A computer system 102 of environment 100, which can include or be embodied as controller 24, is shown including a processing unit (PU) 108 (e.g., one or more processors), an I/O component 110, a memory 112 (e.g., a storage hierarchy), an external storage system 114, an input/output (I/O) device 116 (e.g., one or more I/O interfaces and/or devices), and a communications pathway 118. In general, processing unit 108 can execute program code, such as IC temperature identification program 106, which is at least partially fixed in memory 112. While executing program code, processing unit 108 can process data, which can result in reading and/or writing transformed data from/to memory 112 and/or I/O component 110 for further processing. Pathway 118 provides a communications link between each of the components in environment 100. I/O component 110 can comprise one or more human I/O devices, which enable a human user to interact with computer system 102 and/or one or more communications devices to enable a system user to communicate with the computer system 102 using any type of communications link. To this extent, IC temperature identification program 106 can manage a set of interfaces (e.g., graphical user interface(s), application program interface(s), etc.) that enable human and/or system users to interact with IC temperature identification program 106. Further, IC temperature identification program 106 can manage (e.g., store, retrieve, create, manipulate, organize, present, etc.) data, through several modules contained within a testing system 120.

In any event, computer system 102 can comprise one or more general purpose computing articles of manufacture (e.g., controllers 24) capable of executing program code, such as IC temperature identification program 106, installed thereon. As used herein, it is understood that "program code" means any collection of instructions, in any language, code, or notation, that cause a computing device having an information processing capability to perform a particular function either directly or after any combination of the following: (a) conversion to another language, code or notation; (b) reproduction in a different material form;

and/or (c) decompression. To this extent, IC temperature identification program 106 can be embodied as any combination of system software and/or application software.

Further, IC temperature identification program 106 can include testing system 120. In this case, various modules of testing system 120 can enable computer system 102 to perform a set of tasks used by IC temperature identification program 106, and can be separately developed and/or implemented apart from other portions of IC temperature identification program 106. As used herein, the term "module" means program code that enables computer system 102 to implement the functionality described in conjunction therewith using any solution. When fixed in memory 112 of controller 24 which includes processing unit 108, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of controller 24.

Several modules of testing system 120 are shown in FIG. 4 by way of example. A determinator module 122 can issue instructions, commands, etc. based on data stored within memory 112 of controller 24, or other pieces of information provided thereto. A calculator module 124 can perform mathematical computations, and a comparator module 126 can compare two or more data quantities. Electrical signals or responses transmitted to controller 24 can be translated and/or encoded and stored in memory 112 as test data 128. Each module discussed herein can obtain and/or operate on data from exterior components, units, systems, etc. or from memory 112 of controller 24. In a particular example, the data provided to testing system 120 of IC temperature identification program 106 can be obtained from, e.g., one or more ICs 12 via controller 24. Each IC 12 can include a respective product design, and in some embodiments IC temperature identification program 106 can model numerous distinct components for ICs 12 included as part of the same product or group of products.

Computer system 102 and/or controller 24 can be operatively connected to a heating device 130. Heating device 130 can be in the form of any currently known or later developed instrument for transmitting heat. As non-limiting examples, heating device 130 can be in the form of an industrial furnace, a torch, a resistor, an induction heater, etc. Heating device 130 can be positioned in thermal communication with IC 12 or components thereof. Controller 24 and heating device 130 can be operatively connected to each other by way of a wired connection, wireless network, or other networking scheme and/or instrument. The operative connection between controller 24 and heating device 130 can allow controller 24 to convey instructions to activate, deactivate, and/or control the operation of one or both devices.

Where computer system 102 comprises multiple controllers 24 and/or other computing devices, each device may have only a portion of IC temperature identification program 106 and/or testing system 120 fixed thereon (e.g., one or more modules). However, it is understood that computer system 102 and IC temperature identification program 106 are only representative of various possible equivalent computer systems that may perform a process described herein. To this extent, in other embodiments, the functionality provided by computer system 102 and IC temperature identification program 106 can be at least partially implemented by one or more devices that include any combination of general and/or specific purpose hardware with or without program code. In each embodiment, the hardware and program code, if included, can be created using standard engineering and programming techniques, respectively.

Regardless, when computer system 102 includes multiple controllers and/or other computing devices, the devices can communicate over any type of communications link. Further, while performing a process described herein, computer system 102 can communicate with one or more other computer systems using any type of communications link. In either case, the communications link can comprise any combination of various types of wired and/or wireless links; comprise any combination of one or more types of networks; and/or use any combination of various types of transmission techniques and protocols. Computer system 102 can obtain or provide data, such as data stored in memory 112, using any solution. For example, computer system 102 can generate and/or be used to generate data from one or more data stores, receive data from another system, send data to another system, etc.

Figure 5:
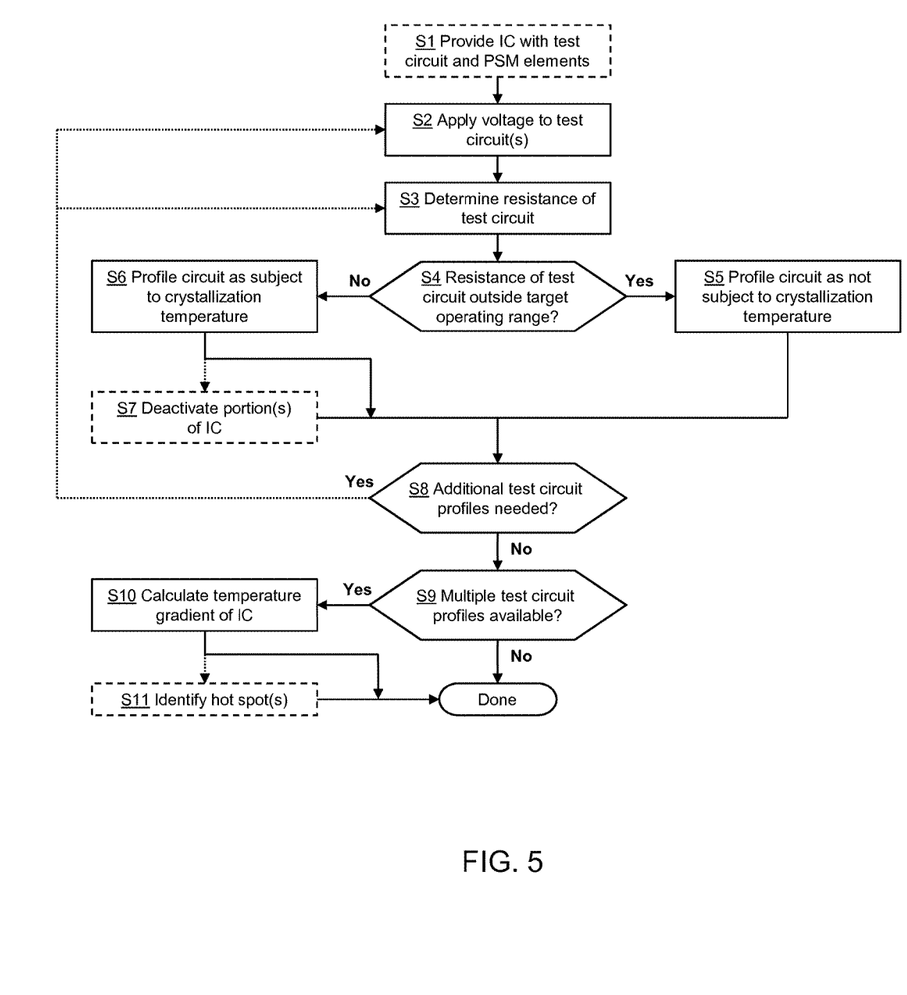
FIG. 5 shows an illustrative flow diagram of processes according to embodiments of the present disclosure.

Turning to FIG. 5, an illustrative flow diagram depicting processes for identifying the operating temperature of an IC is shown. The process flow can include one or more optional process steps, which are shown in phantom and connected by phantom process flow lines. It is understood that some of the process steps discussed herein can be performed by equipment designed or adapted to perform the corresponding function(s) while others can be carried out by components of environment 100 shown in FIG. 4 and discussed herein. Also, it is understood that one or more of the process steps discussed herein can be omitted where applicable. Processes according to the present disclosure can include providing IC 12 which includes one or more test circuits 14 and corresponding PSM elements 16 in step S1. The providing of IC 12 in step S1 can include fabricating IC 12, modifying a pre-existing IC 12 by forming one or more test circuits 14 and/or PSM elements 16 thereon, or other processes for creating IC 12 with one or more test circuits 14. Test circuits 14 can perform various functions during the operation of IC 12, or can perform substantially no function other than being tested to identify operating temperatures of IC(s) 12 as discussed elsewhere herein. In any event, a user can select the composition of PSM elements 16 in test circuits 14 to provide a particular crystallization temperature for each PSM element 16. For example, during step S1, embodiments of the present disclosure can include doping PSM element(s) 16 to include materials which increase or decrease the crystallization temperature. Changing the crystallization temperature of PSM elements 16 can change a target operating range of resistances for test circuit 14.

Fabricated ICs 12 may experience unexpectedly high temperatures during fabrication steps or during operation after being deployed. To determine whether IC 12 has operated above the crystallization temperature, embodiments of the present disclosure can execute steps for identifying operating temperatures of IC 12. At step S2, controller 24 can apply a test voltage to one or more test circuits 14 included within IC(s) 12. The applied test voltage can be preset to a particular value, e.g., approximately 5.0 millivolts (mV).

At step S3, testing system 120 can calculate values of resistance for one or more test circuits 14 in response to controller 24 applying a test voltage. More specifically, controller 24 can measure the electrical response (e.g., the electrical current) of test circuit(s) 14 under the applied test voltage to calculate values of electrical resistance. During application of the test voltage, IC temperature identification program 106 can cross-reference the resistance of test circuit (s) 14 with predicted high and low values of resistance during operation based on, e.g., application of Ohm's Law to portions of test circuit 14. In the example of a 5.0 mV test voltage, PSM element 16 in the amorphous phase may have a resistance of approximately 1.0Ω, thereby causing a current of 5.0 milliamperes (mA) to flow through PSM element 16. From this value of current, calculator 124 can calculate a 1.0Ω resistance which indicates a "high voltage" for a particular test circuit 14 or portion thereof. Where PSM element 16 is in crystalline phase, the same 5.0 mV test voltage can cause a current of approximately 5.0 A to flow though PSM element 16. Calculator 124 can thereby calculate a resistance of approximately 0.001Ω, indicating a "low voltage" across PSM element 16 for test circuit(s) 14 or portion thereof. The values of resistance calculated in step S3 can optionally be stored as test data 128.

At step S4, testing system 120 of controller 24 can determine whether the resistances of test circuits 14 are outside of a target operating range of resistances. The target operating range of resistances can include, e.g., a threshold resistance which corresponds to the properties of PSM element 16 after being crystallized. In an embodiment, comparator 126 of testing system 120 can compare the values of resistance measured or calculated, e.g., from controller 24, with reference values representing "low voltage," "high voltage," etc., for a particular test circuit and/or PSM element. Referring to the example plot of FIG. 2, IC temperature identification program 106 of controller 24 can identify resistances of more than 0.001Ω as corresponding to a high voltage. Where the resistance of test circuit 14 is within the target operating range (i.e., "yes" at step S4), determinator 122 of testing system 120 can identify in step S5 test circuit(s) 14 as not having operated above the crystallization temperature. The resistance of test circuit(s) 14 being outside the target operating range (i.e., "no" at step S4), can at step S6 cause determinator 122 of testing system 120 to identify the corresponding test circuit(s) 14 as having operated above the crystallization temperature.

ICs 12 or portions thereof which controller 24 identifies as having operated above the crystallization temperature may require further service, or may have been subject to unauthorized tampering or modification by an end user or third party. In these situations, a manufacturer can modify IC 12 to "deactivate" at least a portion or particular function of ICs 12 which previously operated above the crystallization temperature. As used herein, the term "deactivate" can refer to a modification process for scrapping, decommissioning, or otherwise disabling functions of IC 12 is temporarily or permanently. Where determinator 122 identifies test circuit (s) 14 as having operated above the crystallization temperature, the flow can optionally proceed to step S7 for deliberately deactivating one or more portions of IC 12. In an embodiment, IC temperature identification program 106 can send instructions or signals to components of IC 12 which are configured to deactivate one or more functions of a product. In an alternative embodiment, IC temperature identification program 106 can instruct (e.g., by transmitting an electrical signal) one or more heating devices 130 to deactivate IC circuit 12 by transferring heat energy to IC 12, to deliberately modify portions of IC 12. For example, IC temperature identification program 106 transmit a current to heating device 130 in the form of a resistor adjacent to PSM element(s) 16 to crystallize PSM element(s) 16 and modify the operation of IC 12. In some embodiments, as discussed elsewhere herein, controller 24 can interact with heating device 130 to program PSM element(s) 16 which act as fuses in IC 12.

As discussed herein, IC temperature identification program 106 can execute temperature identifying operations on test circuit(s) 14 at step S5 (i.e., identified as not having operated above the crystallization temperature) or at step S6 (i.e., identified as having previously operated above the crystallization temperature). In some cases, controller 24 can identify the operating temperature of multiple test circuit(s) 14. Determinator 122 can optionally determine in step S8 whether additional test circuit temperatures are needed, i.e., by identifying non-profiled test circuits 14 from a listing of test circuits 14 to be tested. Where determinator 122 determines that additional identifying of operating temperatures is needed (i.e., "yes" at step S8), the flow can return to step S2 of applying a voltage to other test circuits and determining the resistance of these other test circuits in step S3. Where additional test circuits will not be tested (i.e., "no" at step S8), the flow can continue without more operating temperatures being identified for other test circuits 14 or ICs 12.

At step S9, determinator 122 can determine whether test results from multiple test circuits 14 are available. Where only one test circuit is tested (i.e., "no" at step S9), the process flow can conclude ("Done"). Where multiple test circuits 14 have been tested (i.e., "yes" at step S9), the flow can proceed to step S10 for calculating a temperature gradient of IC 12. As used herein, the term "temperature gradient" refers to a mathematical model, graph, or other illustrative representation IC 12 for demonstrating which test circuits 14 previously operated above the crystallization temperature. Calculator 124 can calculate a temperature gradient of IC 12, e.g., by generating a matrix of data which correlates the temperatures each test circuit 14 with coordinates for the location of each test circuit 14. The calculated temperatures can be stored in memory 112 as a form of test data 128. IC temperature identification program 106 or a separate instrument can convert these values into a graphical display of locations where IC 12 previously operated above the crystallization temperature. The various locations identified via the temperature gradient can correspond to test circuits 14 tested in steps S2-S8.

Determinator 122 in step S11 can optionally identify hot spots of IC 12 based on the calculated temperature gradient yielded from step S10. Controller 24 may identify one or more test circuits 14 as having operated above the crystallization temperature. In this case, testing system 120 of controller 24 can group multiple test circuits 14 together to illustrate hot spots 28 (FIG. 3) where IC 12 operated above the crystallization temperature. The grouping of test circuits 14 into hot spots 28 can be governed, e.g., by rules stored in memory 112 and executed with determinator 122 (e.g., minimum numbers of test circuits 14 with crystallized PSM elements 16 therein, minimum proximity between test circuits 14, etc.). Any hot spots 28 identified with determinator 122 can be added to the visual representation of the calculated temperature gradient and presented to a user, e.g., by way of I/O component 110 and/or I/O device 116. The process flow can end ("Done") after determinator 122 identifies hot spots 28 (if any) in step S11.

Figure 6:
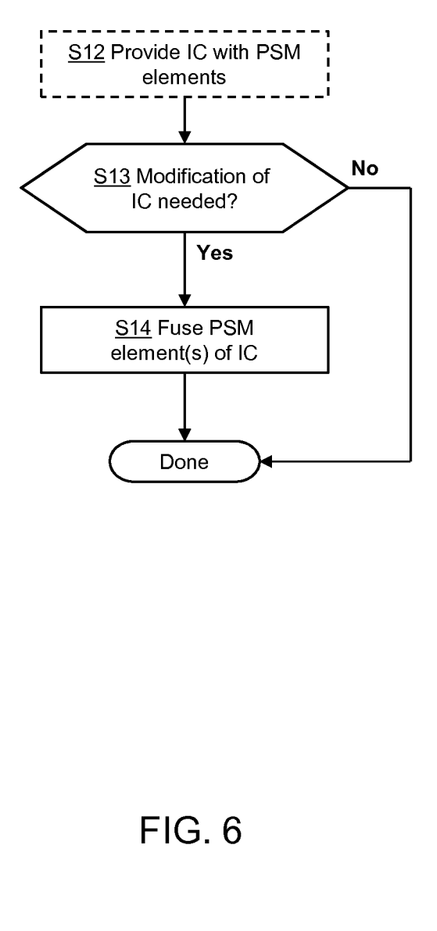
FIG. 6 shows an illustrative flow diagram of processes for modifying an IC according to embodiments of the present disclosure.

Turning FIG. 6, embodiments of the present disclosure can also provide methods for modifying IC 12 to provide different operations, such as an at least partially deactivated mode. For example, controller 24 can modify or deactivate IC(s) 12 by manipulating the operation of particular circuits (e.g., test circuits 14) with PSM elements 16 included therein. Here, PSM elements 16 function as a temperature-programmed fuse as an addition or alternative to serving as testing elements as discussed herein. Thus, modifying IC 12 according to the process flow of FIG. 6 can constitute fusing or otherwise using PSM element(s) 16 as a fuse component. The process flow shown in FIG. 6 can occur before, after, or during processes of other processes discussed herein. The process flow in FIG. 6 can, optionally, be substituted for step S7 (FIG. 5) for deactivating at least one portion of an IC. In addition, methods for modifying IC 12 can occur independently from other methods described herein. The electronic properties of PSM element(s) 16 in IC(s) 12 can vary based on the phase of their material composition. As detailed herein, PSM elements 16 in an amorphous phase may have a greater electrical resistance than in a crystalline phase. PSM elements 16 can change from being in the amorphous phase into being in the crystalline phase after being heated to a crystallization temperature.

Processes for modifying IC 12 can begin with step S12 for providing IC 12 with PSM elements 16 therein. Here, PSM elements 16 can form portions of IC 12 which do not constitute test circuits 14. The providing of IC 12 in step S12 can include fabricating IC 12, modifying a pre-existing IC 12 by forming PSM elements 16 thereon, or other processes for creating IC 12 with one or more PSM elements 16. PSM elements 16 may, incidentally form part of test circuits 14 or can be provided as components of other structures within IC 12. In any event, a user can select the composition of PSM elements 16 to provide a particular crystallization temperature for each PSM element 16. For example, during step S12, embodiments of the present disclosure can include doping PSM element(s) 16 to include materials which increase or decrease the crystallization temperature. Changing the crystallization temperature of PSM elements 16 can the range of temperatures which cause the resistance of PSM elements 16 to change.

At step S13, a user can determine whether to modify IC 12 according to embodiments of the present disclosure. The determination in step S12 can be based on the judgment of a user, and/or automatically with controller 24 after identifying IC(s) 12 as having operated above the crystallization temperature. For example, the determining in step S12 can correspond to the temperature of one or more test circuits 14 as having operated above the crystallization temperature in step S6 (FIG. 5). Where no modification of IC 12 is desired (i.e., "no" at step S13), the process flow can terminate without any action being taken ("Done").

In the event that IC 12 is selected for modification (i.e., "yes" at step S13), the flow can proceed to a step S14, in which IC 12 is fused, e.g., by deliberately heating PSM element(s) 16 to the crystallization temperature. Embodiments of the present disclosure can provide for raising the temperature of PSM element(s) 16 by instructing heating device 130 to transmit heat energy to IC 12. The material composition of IC 12 and components thereof can generally include temperature resistant materials, other than PSM elements 16 therein. In some applications, transferring heat energy to IC 12 can cause PSM element(s) 16 to become substantially crystalline without significantly damaging or affecting the operation of other circuit structures and/or components. After one or more PSM elements 16 substantially crystallize, IC 12 can provide one or more modified operations. The modified circuit operations of IC 12 can be based on, e.g., one or more PSM elements 16 being crystallized and thereby providing a modified (e.g., low voltage) operation as detailed herein. The modified circuit operation provided with PSM element(s) 16 can be a deactivated mode of IC 12 in which one or more electrical functions have been deliberately changed or removed. In other words, the modified circuit operation of PSM element(s) 16 can function as a programmed fuse for some features of IC 12. The fusing of PSM element 16 in step S14 can be an automatic process initiated by controller 24 of IC 12, allowing IC 12 to deactivate or modify itself after being subject to unauthorized tampering, modification, etc. After the fusing of PSM element 16 in process S14, the process flow can conclude ("Done"), with PSM element 16 of IC 12 remaining in a crystalline phase until replaced and/or modified further.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method for identifying an operating temperature of an integrated circuit (IC), the method comprising using a computing device to perform actions including:
   applying a test voltage to a plurality of test circuits embedded within the IC at respective test sites, each of the plurality of test circuits including a phase shift memory (PSM) element therein, wherein each PSM element crystallizes at a crystallization temperature from an amorphous phase having a first electrical resistance into a crystalline phase having a second electrical resistance, the second electrical resistance being less than the first electrical resistance;
   determining whether a resistance of each test circuit of the plurality of test circuits at the test voltage is outside of a respective target operating range; and
   identifying a respective one of the plurality of test circuits as having operated above the crystallization temperature in response to the resistance of the respective test circuit being outside of the respective target operating range.

2. The method of claim 1, wherein each PSM element includes germanium antimony (GeSb).

3. The method of claim 2, wherein each PSM element further includes one of nitrogen (N) or silicon (Si).

4. The method of claim 1, further comprising selecting a material composition of each PSM element before the applying of the test voltage, wherein the material for each PSM element defines the target operating range.

5. The method of claim 1, wherein each PSM element in the crystalline phase remains crystallized below the crystallization temperature.

6. The method of claim 1, further comprising deactivating at least part of the IC in response to one of the plurality of test circuits having operated above the crystallization temperature.

7. The method of claim 1, further comprising calculating a temperature gradient of the IC based on the determining and the identifying of the plurality of test circuits.

8. The method of claim 7, further comprising identifying at least one hot spot of the IC from the calculated temperature gradient, the at least one hot spot including a plurality of adjacent PSM elements identified as having operated above the crystallization temperature.

9. The method of claim 1, wherein the crystallization temperature of each PSM element is approximately 270° C.

10. The method of claim 1, further comprising, before applying the test voltage, doping each PSM element to define the crystallization temperature of each PSM element.

11. The method of claim 1, further comprising deactivating at least part of the IC in response to one of the plurality of test circuits having operated above the crystallization temperature.

12. A system for identifying an operating temperature of an integrated circuit (IC), the system comprising:
a plurality of test circuits embedded within the IC at respective test sites, each of the plurality of test circuits including a phase shift memory (PSM) element therein, wherein each the PSM element crystallizes at a crystallization temperature from an amorphous phase having a first electrical resistance into a crystalline phase having a second electrical resistance, the second electrical resistance being less than the first electrical resistance; and
a controller electrically connected to the plurality of test circuits and configured to perform actions including:
determining a resistance of each test circuit of the plurality of test circuits;
comparing the resistance of each test circuit of the plurality of test circuits with a respective target operating range, and
identifying a respective one of the plurality of test circuits as having operated above the crystallization temperature in response to the resistance of one of the plurality of test circuits being outside of the respective target operating range.

13. The system of claim 12, wherein each PSM element includes germanium antimony (GeSb).

14. The system of claim 13, wherein each PSM element further includes one of nitrogen (N) or silicon (Si).

15. The system of claim 12, wherein each PSM element in the crystalline phase remains crystallized below the crystallization temperature.

16. The system of claim 12, wherein the controller is further configured for calculating a temperature gradient of the IC based on the determining and the identifying of the plurality of test circuits.

17. The system of claim 12, wherein the controller comprises one of a multimeter or a clock generator.

18. The system of claim 12, wherein the controller is further configured for deactivating at least part of the IC in response to one of the plurality of test circuits having operated above the crystallization temperature.

19. The system of claim 16, wherein the controller is further configured for identifying at least one hot spot of the IC from the calculated temperature gradient, the at least one hot spot including a plurality of adjacent PSM elements identified as having operated above the crystallization temperature.

20. The system of claim 19, wherein the controller is further configured for generating a graphical display of locations where the IC operated above the crystallization temperature, based on the calculated temperature gradient.

* * * * *